United States Patent
Nakayasu et al.

(10) Patent No.: US 6,857,319 B2
(45) Date of Patent: Feb. 22, 2005

(54) TEST METHOD OF HYDROSTATIC PRESSURE

(75) Inventors: Masayuki Nakayasu, Himeji (JP); Nobuyuki Katsuda, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/201,277

(22) Filed: Jul. 24, 2002

(65) Prior Publication Data

US 2003/0029244 A1 Feb. 13, 2003

Related U.S. Application Data

(60) Provisional application No. 60/359,899, filed on Feb. 28, 2002.

(30) Foreign Application Priority Data

Jul. 25, 2001 (JP) ........................ 2001-223798

(51) Int. Cl.[7] ................................. G01L 7/10
(52) U.S. Cl. ....................................... 73/730
(58) Field of Search .................. 73/700–756, 299; 340/436, 438; 280/728.1; 180/271; 701/45

(56) References Cited

U.S. PATENT DOCUMENTS 5,205,316 A * 4/1993 Pruett .................... 137/209
6,149,488 A * 11/2000 Stark ..................... 446/220
2002/0000716 A1 1/2002 Chikaraishi et al.

FOREIGN PATENT DOCUMENTS

| JP | 2-158443 A | 6/1990 | |
| JP | 10082888 A | * 3/1998 | ............ G21D/1/00 |
| JP | 2001-108588 A | 4/2001 | |
| JP | 2002-12125 A | 1/2002 | |
| JP | 2002-145004 A | 5/2002 | |

* cited by examiner

*Primary Examiner*—Edward Lefkowitz
*Assistant Examiner*—Jermaine Jenkins
(74) *Attorney, Agent, or Firm*—Birch, Stewart, Kolasch, & Birch, LLP

(57) ABSTRACT

A method for testing hydrostatic pressure of an inflator housing constituting an outer shell container for various inflators, which can evaluate a hydrostatic pressure conveniently is provided. The method comprises the steps of injecting water from a small hole provided in the inflator housing until the pressure inside the inflator housing reaches a predetermined pressure of an evaluation standard, keeping the inflator housing sealed tightly, or comprises the step of increasing the pressure inside the inflator housing to the predetermined pressure while injecting water in the inflator housing, draining the injected water, and drying the interior of the inflator housing.

17 Claims, 1 Drawing Sheet

TEST METHOD OF HYDROSTATIC PRESSURE

This application claims priority on provisional Application No. 60/359,899 filed on Feb. 28, 2002, the entire contents of which are hereby incorporated by reference.

BACKGROUND OF THE INVENTION

1. Field of the Invention

The present invention relates to a method for testing hydrostatic pressure of various kinds of inflators in which a pressurized medium, such as an inert gas, is charged under a high pressure, and a method for manufacturing such various kinds of inflators.

2. Description of Related Art

In an air bag apparatus mounted to an automobile or the like, an inflator which inflates an air bag by an inert gas charged under a high pressure therein or the like, is incorporated. In an inflator of this type, an inert gas such as argon, helium is charged at a high pressure into an inflator housing constituting an outer shell container. Therefore, it is required to test hydrostatic pressure on all products and confirm their safety by the law (High Pressure Gas Safety Law) to secure safety of passengers.

In such a test method, it is required to apply pressure of 1.5 times the internal pressure in an actual product to evaluate the safety thereof. When the charging pressure is 50 to 60 MPa, the hydrostatic pressure in the test is required to be under the high pressure of 75 to 90 MPa. Conventionally, as a method for conducting such a test, the steps of charging gas into an inflator housing and pressurizing the same, or the steps of injecting oil having a high viscosity into an inflator housing and pressurizing the same are employed.

However, in case of charging a gas under a high pressure, a device for charging the gas under such a high pressure is very expensive, and also, if there is a defect, such as bad welding, an inflator housing may break violently due to a gas leakage and may injure a worker.

Also, in case of injecting an oil having a high viscosity, although the safety at a time of the test is high, it is difficult to clean and dry the inside of the inflator housing after the oil is removed, a gas for inflating an air bag is polluted by the remaining oil, and the remaining oil may adversely affect a welded portion.

Further, it is preferable that the testing of hydrostatic pressure is not performed independently of inflator manufacturing processes but incorporated in the manufacturing processes. Therefore, it is also required that a smooth flow of manufacturing processes is not obstructed in view of the whole manufacturing procedure.

SUMMARY OF THE INVENTION

An object of the present invention is to provide a method for testing hydrostatic pressure for confirming the safety of an inflator and a method for manufacturing an inflator in which the hydrostatic pressure testing method is incorporated in a manufacturing procedure.

The present invention provides, as a means for solving the above-described problem, a method for testing hydrostatic pressure of an inflator housing constituting an outer shell container for various inflators, comprising, injecting water from a small hole provided in the inflator housing until the pressure inside the inflator housing reaches a predetermined pressure of an evaluation standard and keeping the inflator housing sealed tightly, or comprising, increasing the pressure inside the inflator housing to the predetermined pressure while injecting water in the inflator housing.

Further, the present invention provides, as a means for solving the above-described problem, a method for testing hydrostatic pressure of an inflator housing constituting an outer shell container for various inflators, comprising, injecting water from a small hole provided in the inflator housing until the pressure inside the inflator housing reaches a predetermined pressure of an evaluation standard and keeping the inflator housing sealed tightly, or comprising, increasing the pressure inside the inflator housing to the predetermined pressure while injecting water in the inflator housing, and draining the injected water.

Further, the present invention provides, as another means for solving the above-described problem, a method for testing hydrostatic pressure of an inflator housing constituting an outer shell container for various inflators, comprising, injecting water from a small hole provided in the inflator housing until the pressure inside the inflator housing reaches a predetermined pressure of an evaluation standard, keeping the inflator housing sealed tightly, or comprising, increasing the pressure inside the inflator housing to the predetermined pressure while injecting water in the inflator housing, draining the injected water, and drying the interior of the inflator housing.

An application range of the method for testing hydrostatic pressure of the present invention is different between a case where an inflator housing subjected to a hydrostatic pressure evaluation is not used as a product and a case where it is used as a product. That is, in the case where the inflator is not using the inflator housing as a product, only the steps of injecting water and holding the water is sufficient. Alternatively, in view of re-use of the inflator, the step of draining water may be added to the above. However, in case of using the inflator housing as a product, it is necessary to dry the interior of the inflator housing in the end. Therefore, the drying step is further added to the above.

Further, the present invention provides, as yet another means for solving the above-described problem, a method for manufacturing an inflator in which a pressurized medium is charged at a high pressure, comprising, injecting water from a small hole provided in the inflator housing until the pressure inside the inflator housing reaches a predetermined pressure of an evaluation standard, keeping the inflator housing sealed tightly, or comprising, increasing the pressure inside the inflator housing to the predetermined pressure while injecting water in the inflator housing, and further comprising, draining the injected water, and drying the interior of the inflator housing.

The method for testing hydrostatic pressure and the method for manufacturing an inflator according to the present invention can be applied to an inflator in which a pressurized medium including nitrogen gas, oxygen gas, and an inert gas, such as argon, helium, and neon, is charged at a high pressure. Specifically, the present invention can be applied to various inflators such as an air bag inflator for a driver side, an air bag inflator for a passenger side, an air bag inflator for a side collision, an inflator for a curtain air bag, an inflator for a knee-bolster, an inflator for an inflatable seat belt, an inflator for a tubular system, and an inflator for a pretensioner.

When the method for testing hydrostatic pressure and the method for manufacturing an inflator, in which the test method of hydrostatic pressure is incorporated in a manufacturing process according to the present invention, are applied, the problem that occurs when gas or oil is used as the conventional method for testing hydrostatic pressure can be solved.

DETAILED DESCRIPTION OF THE INVENTION

Figure 1:
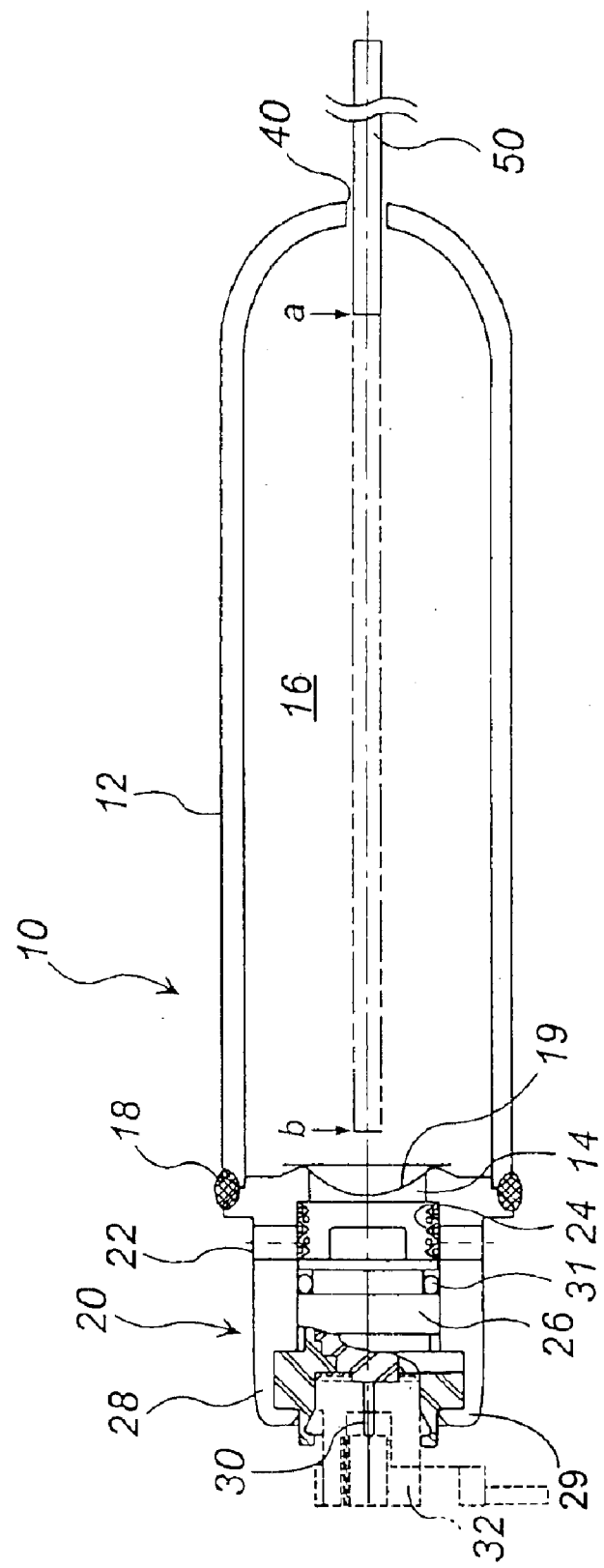
FIG. 1 is an explanatory view of a method for testing hydrostatic pressure of an inflator housing according to the present invention.

An embodiment of a method for testing hydrostatic pressure of an inflator housing of the present invention will be explained with reference to the drawing. FIG. 1 is a sectional view in the longitudinal direction of an inflator 10 for a curtain air bag or an air bag inflator for a side collision (hereinafter, referred to as "an inflator 10") in which a pressurized medium is charged under a high pressure.

First, the inflator 10, which will become a finished product after the hydrostatic pressure evaluation, will be explained. An inflator housing 12 has an opening portion 14 at its one end, closed at the other end, and a pressurized medium comprising an inert gas is charged into an inner space 16 at the pressure of about 60 MPa. The inflator housing 12 has a circular cross-section in a widthwise direction, and the opening portion 14 is also circular.

The inflator housing 12 is nearly closed by swaging or spinning, without closing a small hole 40 which is a charging hole for charging a pressurized medium and is provided at the other end of the inflator housing. After a diffuser portion 20 is connected to the inflator housing 12, an unillustrated seal pin having the same diameter as that of the small hole 40 is fitted into the small hole 40. Then, the pressurized medium is charged from a gap between the small hole 40 and the seal pin, and the inflator housing 12 is welded at a portion of the seal pin to be completely closed.

The diffuser portion 20 is fixed at a connecting portion 18 in the opening portion 14 side of the inflator housing 12 by welding. The diffuser portion 20 has an outer shell formed by a diffuser housing 28. The diffuser housing 28 has a plurality of gas discharging ports 22 for discharging, to an outside, the pressurized medium through the opening portion 14 upon actuation, and it is further provided with a filter 24 made of wire mesh to cover the plurality of discharge ports 22 from the inside thereof. Thereby, the pressurized medium is always discharged outside from the gas discharging ports 22 through the filter 24.

The opening portion 14 of the inflator housing 12 is closed by a rupturable plate 19 mounted to the diffuser portion 20, and before actuation, an inner space 16 of the inflator housing 12 is maintained hermetically at a high pressure. Meanwhile, the gas discharging ports 22 are not closed and in fluid-communication with the outside.

An igniter 26 containing an igniting charge to serve as rupturing means for rupturing the rupturable plate 19 is provided in the diffuser portion 20. This igniter 26 is fixed inside the diffuser housing 28 and mounted to the diffuser portion 20, and it is fixed by crimping an end portion 29 of the diffuser housing 28. Reference numeral 30 is a conductive pin for applying electric current to the igniter 26, reference numeral 31 is an O-ring, and reference numeral 32 represented by a broken line denotes a connector adapted to be connected to the igniter 26 after the inflator 10 is mounted on a vehicle and for supplying power upon activation.

In a manufacturing process of such an inflator 10, generally, after the inflator housing 12 and the diffuser portion 20 are welded at the connecting portion 18, testing of hydrostatic pressure is performed before mounting the igniter 26.

First, water is injected into the inner space 16 through the small hole 40 provided in the inflator housing 12 until the internal pressure of the inflator housing 12 reaches a predetermined pressure which is an evaluation standard (in case of this embodiment, about 60 MPa×1.5=about 90 MPa).

When injecting water, a straw-shaped small-diameter pipe 50 made of stainless steel, aluminum or the like is inserted into the inflator housing 12 from the small hole 40 and then, the injection is performed through the small-diameter pipe 50. It is preferable that water used at this time is pure. Running water, ion-exchanged water or the like can also be used.

Regarding the relationship between the diameter of the small hole 40 and the small-diameter pipe 50, when the diameter of the small hole 40 is 3 mm, the small-diameter pipe having an outer diameter of 1.5 to 2 mm can be used. Also, when injecting water, it is preferable that the small-diameter pipe 50 is inserted until its tip end portion is positioned at the position indicated with "a" or so (at a position near the small hole 40) and then, injection is performed.

After water is injected until it reaches the predetermined pressure, the small-diameter pipe 50 is removed, and the inflator housing is maintained for one minute or so while hermetically closing the small hole 40 by resin or the like, and then the hydrostatic pressure of the inflator housing 12 is evaluated. In this case, whether the internal pressure has reached the predetermined pressure or not can be determined in advance from the volume of the inflator housing 12 and the injecting amount of water.

Also, the following method can be employed as another method. After water is injected in the above-described manner until the interior of the inflator housing 12 is filled with water, the injecting is once stopped and the small-diameter pipe 50 is pulled out. Next, after the small-diameter pipe 50, attached at its tip end with an elastic molded body having a through hole, is pressed so that the through hole is positioned at the small hole 40, injecting of water is restarted. And, after a pressure gauge additionally provided to the small-diameter pipe 50 confirms that the predetermined pressure is obtained, the inflator housing 12 is maintained for one minute or so.

Next, the injected water is drained out. At this time, it is preferable to drain the water through the small-diameter pipe 50 or the small hole 40 (a gap between the small hole 40 and the small-diameter pipe 50) after sealing is removed to insert the small-diameter pipe 50 from the small hole 40 again. In this case, a method includes the steps of inserting the small-diameter pipe 50 so that the tip end portion thereof reaches the position indicated with "b" or so (the position near to the rupturable plate 19) and draining the water from the small-diameter pipe 50 mechanically, the method further includes the steps of charging gas under pressure from the small-diameter pipe 50 and draining the water from the small hole 40, and the steps of charging gas under pressure from the small hole 40 and draining the water from the small-diameter pipe 50 or the like can be employed.

Next, in preparation for the next charging step of a pressurized medium, the interior of the inflator housing 12 is dried by feeding gas therein. When gas is fed, it is preferable to feed a normal temperature gas, heated air or water vapor through the small-diameter pipe 50 to promote drying. Also, heating and drying may be conducted in an oven or the like, as necessary.

Thus, the hydrostatic pressure evaluation is performed during the manufacturing process of the inflator 10, and only inflator housings which are acceptable are transferred to the next-step. Consequently, assembling of other parts such as the igniter 26 is performed to obtain the inflator 10 which is a final product.

EXAMPLE

The present invention will be explained below in detail on the basis of an example, but the present invention is not limited to this example.

Example 1

In the manufacturing process of the inflator 10 shown in FIG. 1, the hydrostatic pressure evaluation of the inflator housing 12 was conducted by the following method. Incidentally, the details of the inflator housing 12 shown in FIG. 1 are as follows:

The quality of the material for the inflator housing 12: iron-base alloy

The thickness of the inflator housing 12: 2 mm

The volume of the inflator housing: 100 ml

The outer diameter of the inflator housing: 30 mm

The diameter of the thin hole 40: 3 mm

The outer diameter of the thin pipe 50: 2 mm

The quality of material for the thin pipe 50: stainless

After the inflator housing 12 and the diffuser portion 20 was connected at the connecting portion 18 by a resistance-welding (or a projection welding, a laser welding), the small-diameter pipe 50 was inserted into the small hole 40 at a manufacturing stage prior to mounting of the igniter 26 so that its tip end was positioned at the position indicated with "a".

Thereafter, running water was injected from the small-diameter pipe 50, the injecting was stopped when the inflator housing was full, and running water was injected further in a state such that the small-diameter pipe 50 attached at its tip end with a rubber-made circular elastic body (having a through hole of a hole diameter of 3 mm) was pressed to meet the through hole and the small hole 40 with each other. When the pressure gauge additionally attached to the small-diameter pipe 50 indicated about 90 MPa, the inflator housing was held for one minute while the pressure was maintained, and it was confirmed that the withstand pressure of the inflator housing 12 satisfied a level required by the Law.

Next, the seal was removed, the small-diameter pipe 50 was inserted until the tip end thereof reached the position indicated with "b" this time, and the running water was drained mechanically by suction.

Then, after air at a normal temperature (20° C.) was fed from the small-diameter pipe 50 for about two minutes at a rate of about 1000 cm$^3$/minute in a state such that the tip end was maintained in the position indicated as "b", the small-diameter pipe 50 was pulled out and the inflator housing was further left in an oven having a temperature of 100° C. for about 10 minutes.

Thereafter, an inert gas was charged from the small hole 40 until the predetermined pressure (60 MPa) was achieved and it was sealed. Finally, necessary parts such as the igniter 26, the connector 32 were attached to the inflator housing so that the inflator 10 was obtained.

What is claimed is:

1. A method for testing hydrostatic pressure of an inflator housing for air bag inflators, comprising:

injecting water through a hole provided in the inflator housing by a first pipe provided in the hole until the inflator housing is filled with water;

pulling the first pipe out of the inflator housing;

attaching a second pipe, including an attaching body provided at a tip end thereof, to the hole by pressing the attached body to the hole;

further injecting water in the inflator housing through the second pipe; and determining whether a predetermined pressure has been maintained inside the inflator housing for a predetermined period of time in said air bag inflator.

2. A method for testing hydrostatic pressure of an inflator housing for air bag inflators, comprising:

injecting water through a hole provided in the inflator housing by a first pipe provided in the hole until the inflator housing is filled with water;

pulling the first pipe out of the inflator housing;

attaching a second pipe, including an attaching body provided at a tip end thereof, to the hole by pressing the attaching body to the hole;

further injecting water in the inflator housing through the second pipe;

determining whether a predetermined pressure has been maintained inside the inflator housing for a predetermined period on time in said air bag inflator; and draining the injected water from the inflator housing.

3. A method for testing hydrostatic pressure of an inflator housing for air bag inflators comprising:

injecting water through a hole provided in the inflator housing by a first pipe provided in the hole until the inflator housing is filled with water;

pulling the first pipe out of the inflator housing;

attaching a second pipe, including an attaching body provided at a tip end thereof, to the hole by pressing the attaching body to the hole;

further injecting water in the inflator housing through the second pipe;

determining whether a predetermined pressure has been maintained inside the inflator housing for a predetermined period of time in said air bag inflator;

draining the injected water from the inflator housing; and drying the interior of the inflator housing.

4. The method for testing hydrostatic pressure of an inflator housing according to any one of claims 1 to 3, wherein the step of injecting water through the hole includes, inserting the first pipe through the hole to inject water via the first pipe, an outer diameter of the first pipe being smaller than an inner diameter of the hole.

5. The method for testing hydrostatic pressure of an inflator housing according to claim 2 or 3, wherein draining step includes, inserting a third pipe to the hole provided in the inflator housing to drain water from at least one of the third pipe and a space between the third pipe and the hole.

6. The method for testing hydrostatic pressure of an inflator housing according to claim 3, wherein drying step includes, inserting a fourth pipe to the hole provided in the inflator housing, and feeding gas to the interior of the inflator housing through the fourth pipe.

7. The method for testing hydrostatic pressure of an inflator housing according to claim 6, wherein the feeding step includes feeding at least one of normal temperature air, heated air, and water vapor.

8. The method for testing hydrostatic pressure of an inflator housing according to any one of claims 1–3, wherein said confirming step includes the step of obtaining an actual pressure by a pressure gauge.

9. A method for manufacturing an inflator in which a pressurized medium under an increased pressure is charged into an inflating housing, comprising:

injecting water from a hole provided in the inflator housing until the pressure inside the inflator housing reaches a predetermined pressure;

sealing the inflator housing;

determining whether the predetermined pressure has been maintained for a predetermined period of time in said air bag inflator;

draining the injected water from the inflator housing; and drying the interior of the inflator housing.

10. The method for manufacturing an inflator according to claim 9, wherein the step of injecting water includes, inserting a first pipe through the hole provided in the inflator housing to inject water via the first pipe, the draining step includes, inserting a third pipe into the hole to drain water from at least one of the third pipe and a space between the third pipe and the hole, and the drying step includes, feeding gas into the interior from a fourth pipe inserted in the hole to dry the interior.

11. The method for manufacturing an inflator according to claim 10, wherein feeding step includes, feeding at least one of normal temperature air, heated air, and water vapor.

12. The method for manufacturing an inflator according to claim 9, wherein said injecting step includes the step of confirming that the predetermined pressure is obtained by a pressure gauge.

13. The method for manufacturing an inflator according to claim 9, wherein the step of injecting water includes the step of injecting water through a second pipe that includes an attaching body provided at a tip end thereof while the attaching body is pressed to the hole.

14. A method for testing hydrostatic pressure of an inflator housing for air bag inflators, comprising:

injecting water from a hole provided in the inflator housing to fill an interior of the inflator housing with the water;

preventing water from escaping from the hole;

continuously providing water inside the inflator housing to increase an internal pressure of the inflator housing to a predetermined pressure; and determining whether the water is leaking from the inflator housing by determining whether a predetermined pressure has been maintained inside the inflator housing for a predetermined period of time in said air bag inflator.

15. A method for testing hydrostatic pressure of an inflator housing for air bag inflators, comprising:

injecting water from a hole provided in the inflator housing to fill an interior of the inflator housing with the water;

preventing water from escaping from the hole;

continuously providing water inside the inflator housing to increase an internal pressure of the inflator housing to a predetermined pressure;

determining whether the water is leaking from the inflator housing by determining whether a predetermined pressure has been maintained inside the inflator housing for a predetermined period of time in said air bag inflator; and draining the injected water.

16. A method for testing hydrostatic pressure of an inflator housing for air bag inflators, comprising:

injecting water from a hole provided in the inflator housing to fill an interior of the inflator housing with the water;

preventing water from escaping from the hole;

continuously providing water inside the inflator housing to increase an internal pressure of the inflator housing to a predetermined pressure;

determining whether the water is leaking from the inflator housing by determining whether a predetermined pressure has been maintained inside the inflator housing for a predetermined period of time in said air bag inflator;

draining the injected water; and drying the interior of the inflator housing.

17. A method for manufacturing an inflator in which a pressurized medium under a high pressure is charged into an inflator housing, comprising:

injecting water from a hole provided in the inflator housing to fill an interior of the inflator housing with the water;

preventing water from escaping from the hole;

continuously providing water inside the inflator housing to increase an internal pressure of the inflator to a predetermined pressure;

determining whether the water is leaking from the inflator housing by determining whether a predetermined pressure has been maintained inside the inflator housing for a predetermined period of time in said air bag inflator;

draining the injected water from the inflator housing; and drying the interior of the inflator housing.

* * * * *